United States Patent [19] [11] 4,035,264
Spoerke et al. [45] July 12, 1977

[54] DEHYDROGENATION CATALYSTS

[75] Inventors: Roger W. Spoerke, Akron; Kenneth J. Frech, Tallmadge, both of Ohio

[73] Assignee: The Goodyear Tire & Rubber Company, Akron, Ohio

[21] Appl. No.: 642,104

[22] Filed: Dec. 18, 1975

Related U.S. Application Data

[62] Division of Ser. No. 508,478, Sept. 23, 1974.

[51] Int. Cl.$^2$ .................... B01J 23/22; B01J 23/26; B01J 23/28; B01J 23/30
[52] U.S. Cl. ............................................... 252/467
[58] Field of Search ............... 252/467; 260/669 R, 260/680 R, 683.3; 423/593, 595

[56] References Cited

U.S. PATENT DOCUMENTS 3,318,966  5/1967  Capp et al. ................... 260/680 R
3,842,132  10/1974 Lo et al. ......................... 260/680 R

*Primary Examiner*—W. J. Shine
*Attorney, Agent, or Firm*—F. W. Brunner; J. Y. Clowney

[57] ABSTRACT

There is disclosed an improved dehydrogenation catalysts prepared from mixtures of $WO_3$ and $V_2O_5$; mixtures of $MoO_3$ and $V_2O_5$ and mixtures of $Cr_2O_3$ or $CrO_3$ and $V_2O_5$ which are heated to temperatures to melt the oxides to form $W(VO_4)_2$, $Mo(VO_4)_2$ and $CrVO_4$ which are then treated with a reductant to form the active dehydrogenation catalytic species, the methods for the preparation of these catalysts and to the improved dehydrogenation processes which can be effected when dehydrogenatable hydrocarbons are in contact with these catalysts.

4 Claims, No Drawings

DEHYDROGENATION CATALYSTS

This is a division of application Ser. No. 508,478 filed Sept. 23, 1974.

This invention is directed to improved dehydrogenation catalysts of the tungsten oxide-vanadium oxide; molybdenum oxide-vanadium oxide and chromium oxide-vanadium oxide types, their preparation and to improve hydrocarbon dehydrogenation processes conducted in contact therewith. More specifically, it is directed to improved dehydrogenation catalysts prepared from mixtures of $WO_3$ and $V_2O_5$; mixtures of $MoO_3$ and $V_2O_5$ and mixtures of $Cr_2O_3$ or $CrO_3$ and $V_2O_5$ which are heated to temperatures of at least 600° C to form $W(VO_4)_2$, $Mo(VO_4)_2$ and $CrVO_4$ which are then treated with a reductant to form the active dehydrogenation catalytic species; the methods for the preparation of these catalysts and to the improved dehydrogenation processes which can be effected when dehydrogenatable hydrocarbons are in contact with these catalysts.

The invention is a catalyst comprising at least one metal vanadate selected from the group of $W(VO_4)_2$, $Mo(VO_4)_2$ and $CrVO_4$ which have been reduced.

The invention is also a catalyst prepared by mixing tungsten oxide, $WO_3$ and vanadium oxide, $V_2O_5$; molybdenum oxide, $MoO_3$ and vanadium oxide, $V_2O_5$ or chromium oxides, $Cr_2O_3$ or $CrO_3$ and vanadium oxide, $V_2O_5$ or mixtures of these oxides of W, Mo and Cr with $V_2O_5$, in amounts that the molar ratio of $WO_3$, $MoO_3$, $CrO_3$ and $Cr_2O_3$ or mixtures thereof to the $V_2O_5$ range from 3 to 1 through 1 to 3, which are heated to a temperature where the mixed oxides react to form tungsten vanadate, $W(VO_4)_2$, or molybdenum vanadate, $Mo(VO_4)_2$ or chromium vanadate, $CrVO_4$ or mixtures thereof, said vanadates being subjected to a reducing agent at a temperature of at least 500° C.

The invention is also a dehydrogenation process comprising placing a dehydrogenatable hydrocarbon under dehydrogenation conditions in contact with a catalyst comprising at least one material selected from the group of $W(VO_4)_2$, $Mo(VO_4)_2$ and $CrVO_4$ wherein the vanadates are reduced.

The improved dehydrogenation catalysts of this invention are usually prepared by mixing tungsten oxide, $WO_3$ and vanadium oxide, $V_2O_5$; molybdenum oxide, $MoO_3$ and vanadium oxide, $V_2O_5$ or chromium oxides, $Cr_2O_3$ and $CrO_3$ and vanadium oxide, $V_2O_5$ or mixtures of $WO_3$, $MoO_3$, $CrO_3$ and $Cr_2O_3$ with $V_2O_5$, in amounts that the molar ratio of these oxides of W, Mo or Cr or mixtures thereof to the $V_2O_5$ range from 3 to 1 through 1 to 3. The mixtures of the oxides of tungsten, molybdenum or chromium or mixtures thereof with the proper amount of $V_2O_5$ are then heated to a temperature to melt the $V_2O_5$. At about 600° to 690° C the melting of $V_2O_5$ occurs and the oxides interact to form tungsten vanadate, $W(VO_4)_2$ or molybdenum vnnadate, $Mo(VO_4)_2$ or chromium vanadate, $CrVO_4$ or in case of mixtures of the oxides of Cr, W and Mo, mixtures of all three vanadates. The temperature of about 600° C is minimum, with about 900° C being the maximum for this heating step. A range from about 675° to about 850° C is more preferred and a range of about 700° to about 800° C is most preferred. The time of heatings of mixtures of the oxides is not critical, times from just a few minutes such as 5-10 minutes or less up to 24 hours have been employed. Of course, the times should be long enough for the oxides to interact to form $W(VO_4)_2$, $Mo(VO_4)_2$ or $CrVO_4$.

After the formation of the $W(VO_4)_2$, $Mo(VO_4)_2$ or $CrVO_4$ or mixtures thereof, these vanadates must be reduced to form the active catalyst. For the reduction step, any known reducing agent may be used. Representative of such known reducing agents are hydrogen, ammonia, hydrazine carbon monoxide, hydrocarbons such as methane, ethane, propane, butane and other hydrocarbons known as reducing agents. Thus, any known reductant may be employed to reduce the $W(VO_4)_2$, $Mo(VO_4)_2$ and $CrVO_4$ or mixtures thereof. Hydrogen is preferred for this reduction step. The reducing step is best carried out at a temperature of about 400° with about 800° C being the practical upper limit, about 550° to about 700° C being more preferred and a range from about 600° to about 675° C being most preferred. The time involved in reduction can vary from less than 5 minutes to 8 hours or more. However, it is preferred to reduce the vanadates from 15 minutes to about 3 hours and more preferred to employ a reducing time from 1/2 to 1 hour. This reducing treatment converts the $W(VO_4)_2$, $Mo(VO_4)_2$ and $CrVO_4$ into much improved catalysts for the dehydrogenation of dehydrogenatable hydrocarbons as can be observed in the examples disclosed later in the specification.

As will be observed from the actual dehydrogenation, the reduction of the tungsten, molybdenum and chromium vanadates results in an improved process. Compare run 5 with run 1, Experiment I, and run 6 with runs 1, 2 and 3, Example II. One of the interesting and advantageous features of this process is that the catalysts of the invention remains activated for very long periods of use, due to the fact that hydrogen is produced and this hydrogen activates or reduces these vanadates continuously. Also the use of a hydrocarbon as a diluent tends to produce hydrogen in the dehydrogenation process which is also useful to reduce the catalysts of the invention.

Any dehydrogenatable hydrocarbon may be contacted with the catalysts of this invention under dehydrogenation conditions to provide an improved dehydrogenation process.

Representative of some of the hydrocarbon dehydrogenation processes, which the catalysts of this invention will provide an improvement in, are those in which paraffins are dehydrogenated to olefins, representative of which are propane to propylene, n-butanes to n-butenes, isobutanes to isobutenes, n-pentanes to n-pentenes, isopentanes to isopentenes, dimethylbutanes to dimethylbutenes, methylbutanes to methylbutenes, ethylbutanes to ethylbutenes, methylpentanes to methylpentenes, dimethylbutane to dimethylbutenes; also the dehydrogenation of ethylbenzene to styrene and isopropylbenzene to a-methylstyrene; olefins to diolefins, representative of which are butenes to butadienes, isopentenes or isoamylenes to isoprene, n-pentenes to pentadienes, methylbutenes to methylbutadienes, dimethylbutenes to dimethylbutadienes, such as 2,3-dimethylbutene to 2,3-dimethylbutadiene, methylpentenes to methylpentadienes, ethylbutenes to ethylbutadiene.

In the dehydrogenation of the dehydrogenatable hydrocarbons in contact with the improved catalysts of this invention, the operating parameters may vary widely. These operating variables are usually governed by the particular hydrocarbon being dehydrogenated as well as other factors including the conversion desired, the selectivity desired, the contact between the active catalyst and the hydrocarbon, whether a diluent and what diluent is employed. All the factors are known to those skilled in the art who will be able to consider these operating parameters and optimize the process. As a guide, however, it has been found that the residence time, the time the hydrocarbon to be dehydrogenated is in contact with the catalyst, may vary from about 0.01 second to about 20 minutes with about 0.1 to 5 seconds being more preferred. The temperatures which are suitable for these dehydrogenations may vary from about 200° up to about 800° C with about 300° to about 650° C being more preferred.

Inert diluents may be employed in the dehydrogenation processes of this invention, particularly, as a heat transfer medium. If an inert diluent is desired, any inert material which will not adversely affect the dehydrogenation process of the catalysts may be employed. Representative of such diluents are water, methane, ethane, propane, nitrogen, carbon monoxide and carbon dioxide and other hydrocarbons not adversely affecting the dehydrogenation process. When a diluent is employed the molar ratio of diluent to hydrocarbon feed can be up to 20/1 or more but it has been found that no advantage is obtained if the molar ratio is above 5/1 or 6/1. It is usually best to keep the diluent to hydrocarbon molar ratio at about 3/1 to 4/1. It is particularly useful to use a hydrocarbon as the diluent under certain conditions. For instance, if 1- or 2-butene were being dehydrogenated to butadiene, one could use butane as a diluent or heat transfer medium and the butane would undergo some dehydrogenation to produce more butenes, thus, providing an added benefit. On the other hand, one would not want to employ a 3 carbon or 5 carbon hydrocarbon such as propane or pentane because of the added problem in separating the various components of the effluent. In some cases, it might be better to employ water or methane as the diluent due to the ease of their separation from the products of the dehydrogenation. Therefore, one could envision a process wherein the dehydrogenatable hydrocarbon is an olefin and in which the diluent would be a paraffin having the same number of carbon atoms and the same molecular configuration as does the olefin which is to be dehydrogenated. For instance, if one were dehydrogenating 2,3-dimethyl-butene-1, or -2, to form 2,3-dimethyl-butadiene-1,3, it would be advantageous to employ as a diluent 2,3-dimethylbutane.

If desired, these catalysts may also be employed with a conventional support material. Representative of which are alumina, silica, silica-alumina, titania, magnesia, zirconia and the metal carbonates of aluminum, silicon, magnesium, titanium and zirconium. If a support is to be employed, the oxides or carbonates of aluminum, silicon, magnesium, titanium and zirconium can be mixed with the mixtures of tungsten oxide and vanadium oxide, mixtures of molybdenum oxide and vanadium oxide and mixtures of chromium oxide and vanadium oxide in amounts so that in the final catalyst there is at least 10 percent by weight of tungsten, molybdenum or chromium vanadates, the remaining portion being the weight of the support material mentioned above. It is usually preferred, however, to employ the reduced tungsten, molybdenum and chromium vanadates or in mixture with each other as the catalyst, as the use of a support has not shown any great advantage.

This invention is further illustrated by reference to the following examples which are intended to be representative and not in any way limitative of the scope of the invention.

EXAMPLE I

A series of experiments were conducted as follows:

Equal molar quantities of $Cr_2O_3$ and $V_2O_5$ were mixed thoroughly together and placed in a furnace in an air atmosphere and heated overnight at 750° C. The $CrVO_4$ formed was reduced to particles ranging in size from one sixteenth to one eighth inch. Portions of this $CrVO_4$ were placed in a microflow reactor. The $CrVO_4$ was treated with a flow of hydrogen at 600° C for 30 minutes. At this time the particular hydrocarbon recited in Table 1 was fed to the reactor at the rate and at the temperature recited in Table 1. The results of these dehydrogenations are also reported in Table 1. Mole percent yield is mole percent of the diolefin obtained corresponding to olefin feed. Mole percent conversion is the mole percent of the olefin converted and percent selectivity is obtained by dividing the mole percent yield by the mole percent conversion. In each of these dehydrogenations the temperature was 575° C and the residence time was 0.5 second. In run 5 the $CrVO_4$ received no hydrogen pretreatment. In run 6 the reactor contained no catalyst at all. Runs 5 and 6 are for comparative purposes and do not illustrate the invention. All analysis are by conventional gas chromatographic techniques.

TABLE 1

| Run No | Reactant | Mole % Yield | Mole % Conv | % Selectivity |
|---|---|---|---|---|
| 1 | 2-pentene | 32 | 37 | 87 |
| 2 | 2-methyl-2-butene | 31.4 | 33 | 95 |
| 3 | 2,3-dimethyl-2-butene | 63.6 | 64 | 99 |
| 4 | 2-butene | 21 | 23 | 92 |
| 5(a) | 2-pentene | 8 | 16 | 50 |
| 6(b) | 2-pentene | 3 | 6 | 50 |

(a) $CrVO_4$ not pretreated with hydrogen
(b) no catalyst employed at all

As can be observed, the dehydrogenation reported in Table 1 illustrates that the catalysts of this invention provide an improved olefin dehydrogenation process, particularly note what advantages are gained by the pretreatment of $CrVO_4$ with hydrogen (compare run 1 with run 5).

EXAMPLE II

A series of runs were conducted in a manner similar to those of Example I except that pentane was the feed stock instead of an olefin. The catalysts were prepared in the identical manner as in Example I. Certain control runs were made for comparative purposes. Run 4 $Cr_2O_3$ alone was used as the catalyst; run 5, $V_2O_5$ alone, was used as the catalyst and run 6 the $CrVO_4$ was not treated with hydrogen. The conditions of the dehydrogenations were 575° C and the residence time was 0.5 second except run 2 which was 1.5 seconds. The results are reported in Table 2 in which the mole percent conversion and the mole percent selectivity are the same as in Table 1. The mole percent yield reports both the pentene and pentadiene formed combined.

TABLE 2

| Run No | Reactant | Mole % Yield | Mole % Conv | % Selectivity |
|---|---|---|---|---|
| 1 | Pentane | 25 | 35 | 71 |
| 2 | Pentane | 28 | 42 | 66 |
| 3 | Propane | 35 | 38 | 92 |
| 4(a) | Pentane | 16 | 19 | 84 |
| 5(b) | Pentane | 14 | 18 | 77 |
| 6(c) | Pentane | 10 | 15 | 73 |

(a)$Cr_2O_3$ only as catalyst
(b)$V_2O_3$ only as catalyst
(c)$CrVO_4$ not pretreated with hydrogen As can be observed, the dehydrogenation reported in Table 2 illustrates that the catalysts of this invention provide an improved paraffin dehydrogenation process, particularly note the advantages gained when the $CrVO_4$ is pretreated with hydrogen. Also note the improvement in mole percent yield obtained by hydrogen pretreated $CrVO_4$ over the $Cr_2O_3$ and $V_2O_5$ alone as the catalyst in these dehydrogenations.

While there has been disclosed the reaction of $MoO_3$, $WO_3$, $Cr_2O_3$ and $CrO_3$ with $V_2O_5$, those skilled in the art may employ other oxides of W or Mo which may exist to react with $V_2O_5$ to form the vanadates of molybdenum and tungsten.

While certain representative embodiments and details have been shown for the purpose of illustrating the invention, it will be apparent to those skilled in this art that various changes and modifications may be made therein without departing from the spirit or scope of the invention.

What is claimed is:

1. A composition of matter comprising at least one metal vanadate selected from the group of tunsten vanadate $W(VO_4)_2$, molybdenum vanadate $Mo(VO_4)_2$, and chromium vanadate $CrVO_4$, said metal vanadates being reduced by exposure to at least one reducing agent selected from the group consisting of hydrogen, ammonia, hydrazine, carbon monoxide, methane, ethane, propane and butane, at a temperature of about 400° to about 800° C., for a period of about 5 minutes to about 8 hours.

2. A composition of claim 1 in which the metal vanadate is chromium vanadate.

3. A composition of claim 1 in which the metal vanadate is exposed to hydrogen for about 15 minutes to 3 hours at a temperature of 550° to about 700° C.

4. A composition of claim 3 in which the metal vanadate is chromium vanadate.

* * * * *